US009095671B2

(12) United States Patent
Feriani et al.

(10) Patent No.: US 9,095,671 B2
(45) Date of Patent: Aug. 4, 2015

(54) SELF-SENSING DISPENSING DEVICE

(71) Applicant: Henkel AG & Co. KGaA, Duesseldorf (DE)

(72) Inventors: Amir Feriani, Auvernier (CH); Cedric Zaugg, Neuchatel (CH); Jean-Paul Sandoz, Cormondreche (CH); Joseph Hess, Bevaix (CH)

(73) Assignee: Henkel AG & Co. KGaA, Duesseldorf (DE)

( * ) Notice: Subject to any disclaimer, the term of this patent is extended or adjusted under 35 U.S.C. 154(b) by 103 days.

(21) Appl. No.: 13/892,365

(22) Filed: May 13, 2013

(65) Prior Publication Data
US 2013/0248558 A1 Sep. 26, 2013

Related U.S. Application Data

(62) Division of application No. 12/705,450, filed on Feb. 12, 2010, now abandoned.

(30) Foreign Application Priority Data

Feb. 10, 2009 (EP) ..................................... 09152483

(51) Int. Cl.
B05B 12/12 (2006.01)
A61M 15/00 (2006.01)
(Continued)

(52) U.S. Cl.
CPC .......... A61M 15/0091 (2013.01); A47K 5/1217 (2013.01); A61L 2/22 (2013.01); A61L 9/14 (2013.01); A61M 11/00 (2013.01); A61M 15/0085 (2013.01); B05B 12/12 (2013.01); B05B 12/122 (2013.01);
(Continued)

(58) Field of Classification Search
USPC .................................. 222/52, 180–181.3, 196
See application file for complete search history.

(56) References Cited

U.S. PATENT DOCUMENTS 3,273,752 A 9/1966 Horeczky
4,218,013 A * 8/1980 Davison .......................... 239/74
(Continued)

FOREIGN PATENT DOCUMENTS

EP 0923957 A1 6/1999
EP 1129741 A2 9/2001
(Continued)

OTHER PUBLICATIONS

European Search Report (EP 09152483) dated Mar. 8, 2009.

Primary Examiner — Donnell Long
(74) Attorney, Agent, or Firm — P. Scott Smith

(57) ABSTRACT

A self-sensing dispensing device comprising: power supply means, a liquid dispensing element comprising an actuator and a dispensing aperture through which liquid is to be dispensed by activation of the actuator, electronic control means operable to control said actuator, liquid supply means for connecting with a liquid reservoir to supply liquid to said liquid dispensing element, valving means for allowing or blocking liquid to flow from said reservoir to said liquid dispensing element, wherein said actuator is operable to execute in itself at least a dispensing function and a detecting function, the detecting function detecting at least characteristics external to the self-sensing dispensing device and causing said actuator to generate a command signal, and wherein said electronic control means is operable to control said valving means and said actuator based on the reception of said command signal.

11 Claims, 7 Drawing Sheets

(51) Int. Cl.
*A47K 5/12* (2006.01)
*A61L 2/22* (2006.01)
*A61L 9/14* (2006.01)
*A61M 11/00* (2006.01)
*B05B 17/06* (2006.01)
*A61M 16/00* (2006.01)
*B05B 1/30* (2006.01)
*B05B 17/00* (2006.01)

(52) U.S. Cl.
CPC ........ *B05B 17/0607* (2013.01); *B05B 17/0684* (2013.01); *A61L 2202/14* (2013.01); *A61L 2209/11* (2013.01); *A61L 2209/111* (2013.01); *A61L 2209/132* (2013.01); *A61M 2016/0018* (2013.01); *A61M 2016/0021* (2013.01); *A61M 2016/0039* (2013.01); *A61M 2205/14* (2013.01); *A61M 2205/8206* (2013.01); *B05B 1/3053* (2013.01); *B05B 17/0646* (2013.01)

(56) References Cited

U.S. PATENT DOCUMENTS

| | | | | |
|---|---|---|---|---|
| 4,659,014 A | * | 4/1987 | Soth et al. | 239/102.2 |
| 4,839,039 A | * | 6/1989 | Parsons et al. | 210/143 |
| 5,301,873 A | * | 4/1994 | Burke et al. | 237/53 |
| 5,487,378 A | * | 1/1996 | Robertson et al. | 128/200.16 |
| 6,405,934 B1 | | 6/2002 | Hess et al. | |
| 6,820,821 B2 | | 11/2004 | Linstedt et al. | |
| 6,978,941 B2 | * | 12/2005 | Litherland et al. | 239/4 |
| 6,991,184 B2 | * | 1/2006 | Romaine | 239/318 |
| 7,155,758 B1 | * | 1/2007 | Berke et al. | 4/675 |
| 7,690,395 B2 | * | 4/2010 | Jonte et al. | 137/624.11 |
| 7,775,459 B2 | * | 8/2010 | Martens et al. | 239/102.2 |
| 8,191,732 B2 | * | 6/2012 | Ehlert et al. | 222/1 |
| 8,197,762 B2 | * | 6/2012 | Gasper | 422/125 |
| 2003/0146300 A1 | | 8/2003 | Denyer et al. | |
| 2004/0004133 A1 | | 1/2004 | Ivri et al. | |
| 2007/0216256 A1 | | 9/2007 | Vogeley | |
| 2008/0110453 A1 | | 5/2008 | Ross et al. | |

FOREIGN PATENT DOCUMENTS

| | | |
|---|---|---|
| EP | 1681001 A2 | 7/2006 |
| EP | 1043162 B1 | 3/2007 |
| WO | 2006/059059 A1 | 6/2006 |

* cited by examiner

Data Acquisition and Processing:

Data Acquisition and Processing:

SELF-SENSING DISPENSING DEVICE

FIELD OF THE INVENTION

The present invention generally relates to a self-sensing dispensing device, suitable for dispensing liquid substances, such as by activating a flow or a spray of droplets. Such device normally contains a dispensing body on a support part, in particular, a spout or a nozzle body of a liquid droplet spray device which dispenses a liquid substance from the device through the dispensing body. Such activation may be carried out by valving means to allow a flow and/or by pumping or pressurizing means. Such activation may further be carried out by a piezoelectric actuator used as a vibrating element for causing the liquid to vibrate so to be accelerated and expelled. A typical device further may consist of elements such as a liquid space, liquid feed and fluid interface to a reservoir, a reservoir as well as electrical connections between the vibrating element and a corresponding electronic circuitry. The liquid may be for example an ambient fragrance, a perfume, an insecticide, a fungicide, a fabric softener, an aromatherapy essence, a cleaning solution, a lotion, cream, emulsion, aqueous based liquids and flammable or combustible liquids.

BACKGROUND OF THE INVENTION

Such dispensing bodies are sometimes called spouts, aperture plates, nozzle arrays, dosing apertures, orifice plates, vibratable membranes, atomizer, vibrating plate, dosing aperture arrangements, aerosol generators and the like. Such terms are hence to be understood as being interchangeable throughout the present document.

In fact such dispensing bodies and liquid dispensing devices are well known. For example see the document EP 1 129 741 in the name of the present Applicant. This document describes a dispensing device for spraying liquid and has a top substrate formed of a main body and of a nozzle body. The nozzle body contains a nozzle array of liquid droplet outlet means allowing a liquid substance contained in the liquid droplet spray device to exit the device, in this case as a spray of droplets. A piezoelectric actuator is used to cause the liquid to undergo a vibration so as to generate the droplet spray.

Generally, such piezoelectric actuator is driven so as to oscillate at or near an appropriate frequency to improve energy efficiency.

The document EP 1 043 162 describes an inkjet apparatus having a liquid detection method using an infrared detector to determine if liquid has passed through a spray path or not. Control means are provided to adjust the spraying itself.

The document US 2007/0216256 describes a drive control circuit for a piezoelectric activated pump. By measuring the internal impedance of the piezoelectric actuator, it is possible to control the operation frequency.

Document US2003/0146300 describes a nebulizer for nebulizing a substance and a reservoir having a metering chamber arranged so as to feed a substance to be nebulized from the nebulization device and a second chamber arranged to hold and retain any of this substance in excess of the volume held in the metering chamber. The device allows detecting the ejection of a unit dose.

However, a simplified and reliable controlled activation and deactivation of the actuator would be useful if the actuator could function by itself so as also to detect dispensing conditions and to control and/or monitor liquid dispense actuation.

It is, therefore, an object of the present invention to provide an innovative dispensing device that overcomes the inconveniences and limitations presented by the prior art documents.

Thus, the present invention concerns a dispensing device fulfilling these objectives efficiently which may be obtained in a relatively simple and inexpensive manner, as defined in the appended claims. The device is further capable of indirectly triggering and monitoring itself.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

Self-sensing liquid cleaner or fabric softener dispensing device comprising: power supply means; a liquid dispensing element comprising an actuator and a dispensing aperture through which liquid is to be dispensed by activation of the actuator; electronic control means operable to control said actuator, liquid supply means for connecting with a liquid reservoir to supply liquid from said reservoir to said liquid dispensing element; valving means for allowing or blocking liquid to flow from said reservoir through said liquid supply means to said liquid dispensing element, wherein said actuator is operable to execute in itself at least a dispensing function and a detecting function, the detecting function detecting at least characteristics external to the self-sensing dispensing device and causing said actuator to generate a command signal, and wherein said electronic control means is operable to control said valving means and said actuator based on the reception of said command signal.

BRIEF DESCRIPTION OF THE DRAWINGS

The present invention will hereinafter be described in conjunction with the following drawing figures, wherein like numerals denote like elements.

FIG. 1b1 shows an example of a priming system for a self-sensing piezoelectric dispensing device in the first embodiment;

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Thanks to the features of the self-sensing dispensing device according to the present invention, it is possible to reliably control the operation of the liquid dispensing device, and this without requiring any separate sensor.

Other features and advantages of the self-sensing dispensing device according to the present invention will become clear from reading the following description, which is given solely by way of a non-limitative example thereby referring to the attached drawings.

An example of preferred embodiments will now be described while referring to the figures. Generally, the self-sensing dispensing device according to the present invention is used to control the operation of an actuator in a liquid dispensing device.

In the first embodiment, a self-sensing piezoelectric dispensing device is used as a water flow detector arranged close to a showerhead of a shower apparatus. By detecting a flow of water, a cleaning, disinfecting or fragrancing formulation, or the like, may be dispensed from the self-sensing piezoelectric dispensing device. This may be done for example by way of a spray of droplets, i.e. in such a case the dispensing device is an atomizer or liquid droplet spray device.

Shower cleaning devices are known as such. For example, the document U.S. Pat. No. 6,820,821 discloses an automated sprayer for spraying the walls of a bath and shower enclosure with a cleanser. The sprayer has a housing that can be mounted inside the shower enclosure. A tube extends downwardly along a longitudinal axis through which the cleanser can pass. A motorized head disposed beneath the tube can be rotated about the axis for metering cleanser from the bottle and spraying cleanser outward. The sprayer includes a motion sensor to prevent spraying if someone is present in the shower.

Clearly such device requires a separate sensor to allow for triggering of the desired operation (spraying of cleaner) making the system more vulnerable and more expensive.

Thanks to the features of the present invention, a separate sensor can be avoided, as it is the piezoelectric actuator itself that functions as a sensor. Therefore, reliability can be improved, as there are fewer parts prone to malfunctioning.

Figure 1A:
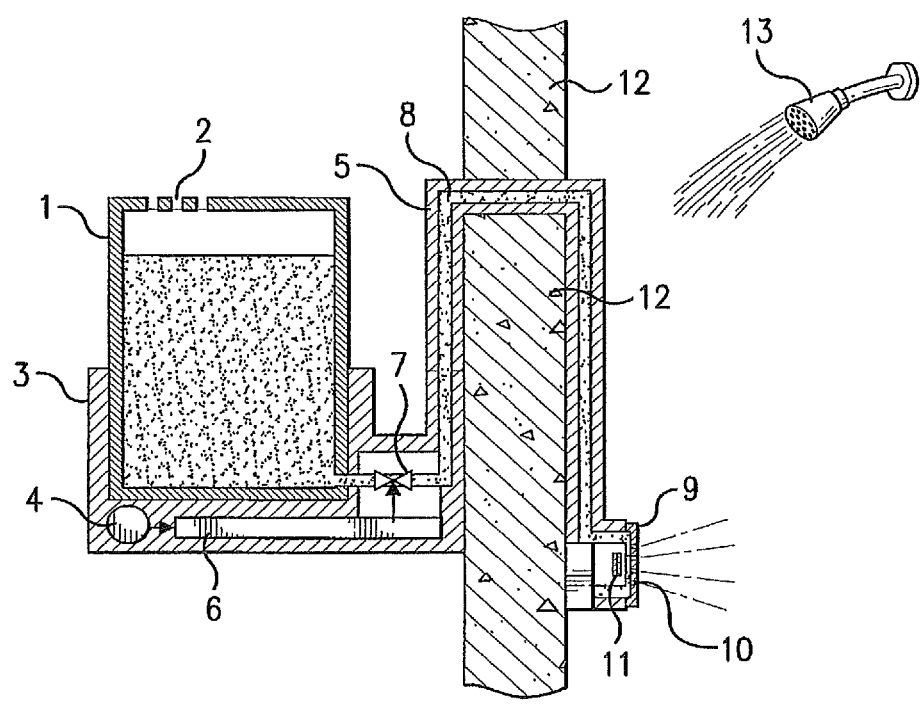
FIG. 1a shows a first example of a self-sensing piezoelectric dispensing device in a first embodiment according to the present invention used in a water flow detector of a shower apparatus.

A first example of the first embodiment is shown in FIG. 1a where a pressurized cleaner tank 1 is provided for containing a liquid. A venting hole 2 is advantageously provided with a hydrophobic membrane to ensure correct priming by tank over-pressuring and also to ensure correct emptying of the tank.

Figure 1B:
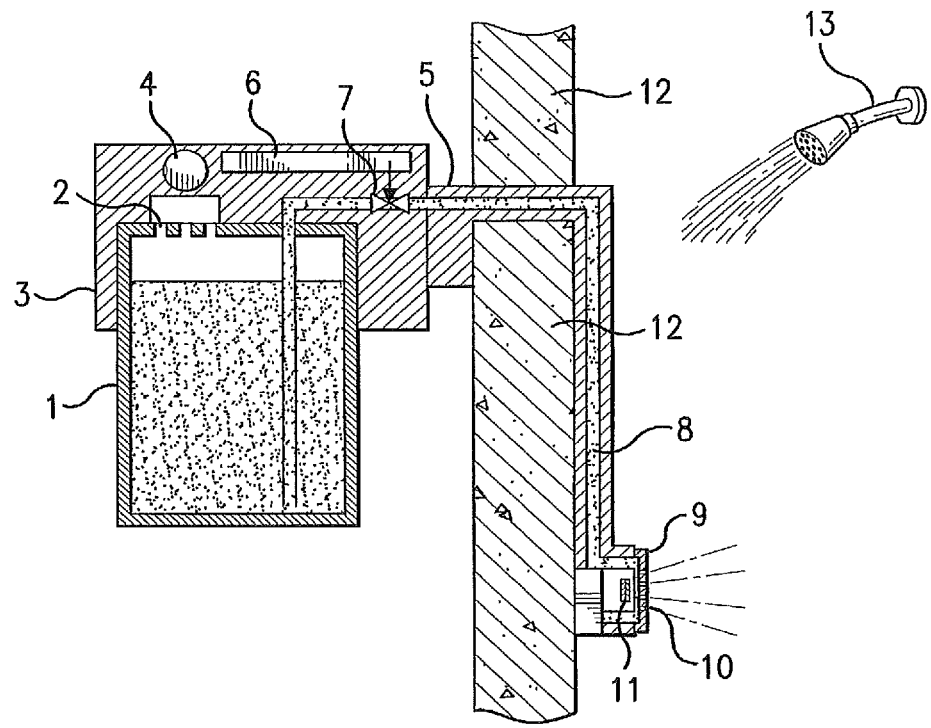
FIG. 1b shows a second example of a self-sensing piezoelectric dispensing device in the first embodiment.
Figures 1, 1B:
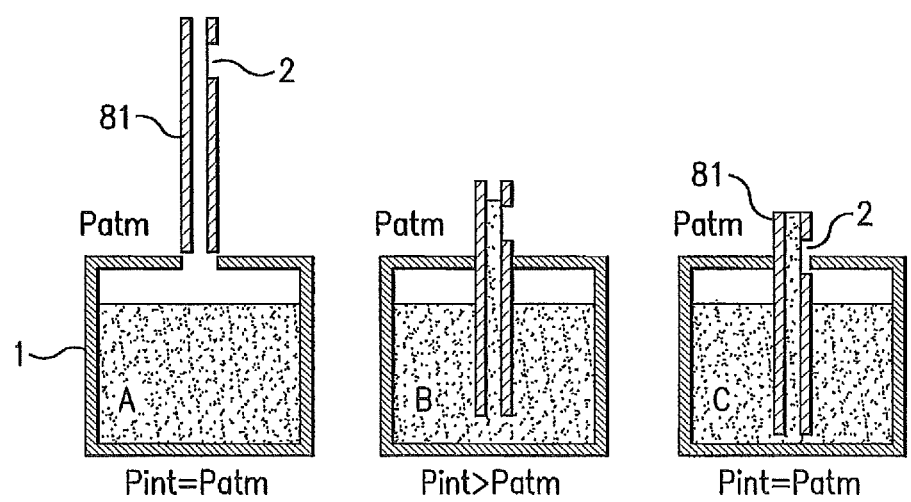

Alternatively, as shown in FIG. 1b1, instead of a hydrophobic membrane, a liquid feed conduit 81 having a cut-out section acting as a venting hole 2 can be used to pressurize the liquid and to vent the tank and feed the liquid to an inlet channel 8. As shown in this Figure, first this liquid feed conduit 81 is ready to be inserted into the tank (A). At this stage, the pressure $P_{int}$ in tank 1 is equal to the atmospheric pressure $P_{atm}$. Next, it enters the tank (B), so that the internal pressure $P_{int}$ becomes greater than $P_{atm}$. Finally it arrives at the bottom of the tank such that the venting hole allows for release of air (C) so that $P_{int}$ equals again $P_{atm}$.

Tank 1 is placed in a housing 3 fitted to a shower apparatus having a showerhead 13. Housing 3 further contains a battery 4 and appropriate electronic control means 6 for activating and deactivating a dispensing element, here a liquid spray head 9. Liquid spray head 9 is mounted on a support, for example a wall 12 in the vicinity of showerhead 13. Liquid spray head 9 comprises a piezoelectric actuator 11 and an aperture plate or nozzle head 10 having one or more outlet nozzles through which the liquid cleaning solution is expelled as a spray of droplets, in a manner well known to a person of the art. An inlet channel 8 is provided to supply liquid from tank 1 to spray head 9. Inlet channel 8 may be mounted to support 12 by way of a clip 5. Access from tank 1 to spray head 9, through inlet channel 8, may be controlled by valving means, for example an electro-valve 7, suitably arranged between the tank and the spray head, and controlled by electronic control means 6.

Figure 1C:
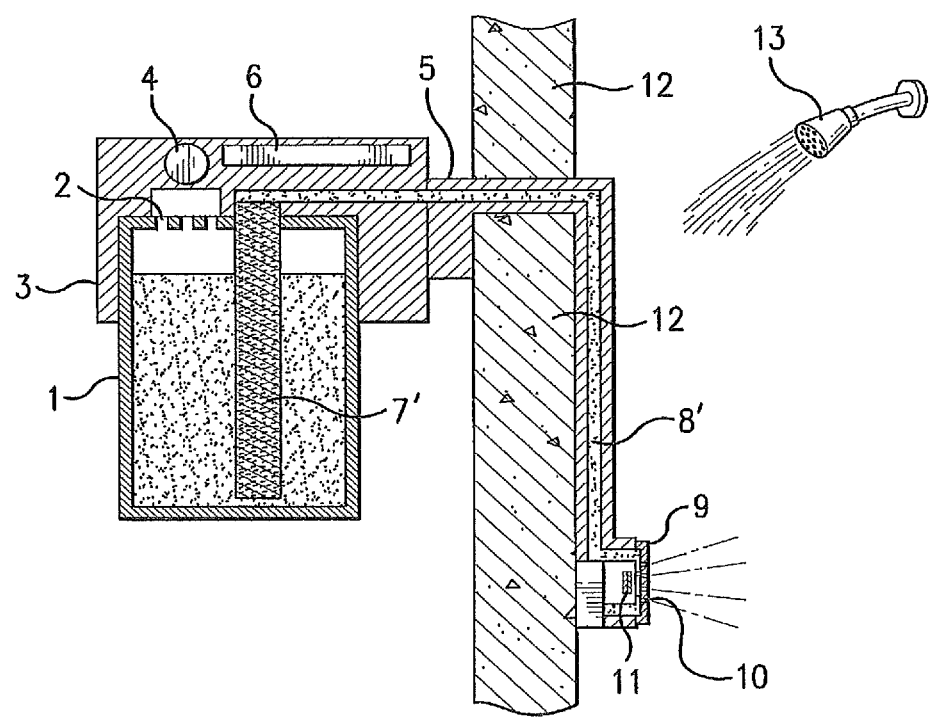
FIG. 1c shows a third example of a self-sensing piezoelectric dispensing device in the first embodiment.

As the person skilled in the art will readily recognize there can be one or more tanks and one or more liquids. Electrovalve 7 can be a one way or multi-way valve. There can be one or several liquid spray heads. Also the tank arrangement and the liquid spray arrangement may be side by side on a surface instead of on different sides of a wall such as shown in FIGS. 1a, 1b and 1c.

As such, any liquid supplied to spray head 9 is put into vibration by piezoelectric actuator 11 so that ultrasonic energy thus created acts on liquid in spray head 9 to cause it to be ejected as a spray of droplets through the nozzle(s) 10, in a manner known to the skilled person.

Indeed, the piezoelectric actuator is operable to execute at least a dispensing function and a detecting function. The dispensing function may be triggered by an electronic control signal from electronic control means 6 for vibrating the piezoelectric actuator, whereby the ultrasonic energy is transmitted to the liquid so as to allow for vibration thereof, thereby resulting in the dispensing of the liquid from said dispensing element through the nozzle(s) 10. The detecting function is used to detect at least characteristics external to the dispensing device and results in a perturbation of the piezoelectric actuator. This perturbation generates an electronic signal, which may be detected by electronic control means 6, and thus may constitute a command signal of electronic control means 6 for controlling valving means 7 and spray head 9.

Figure 1D:
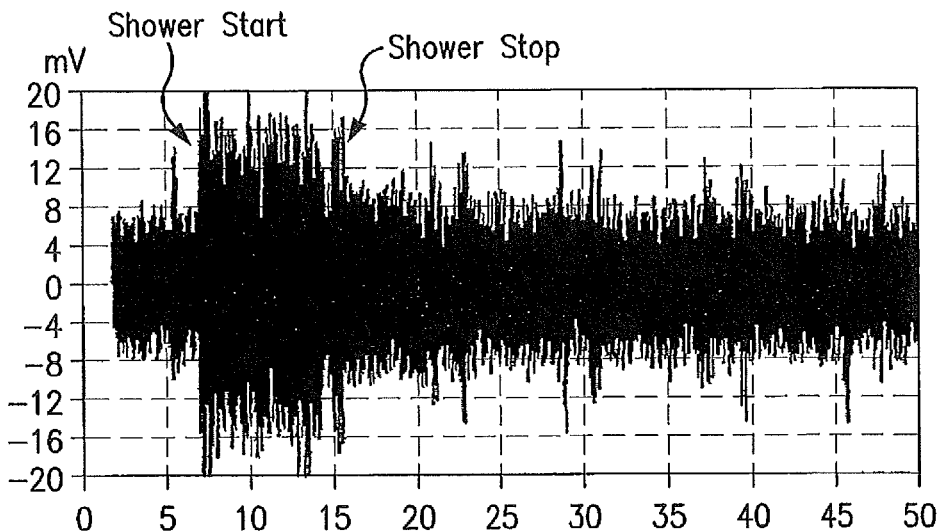
FIGS. 1d and 1e show examples of signals used in a water flow detection in the first embodiment.
Figure 1E:
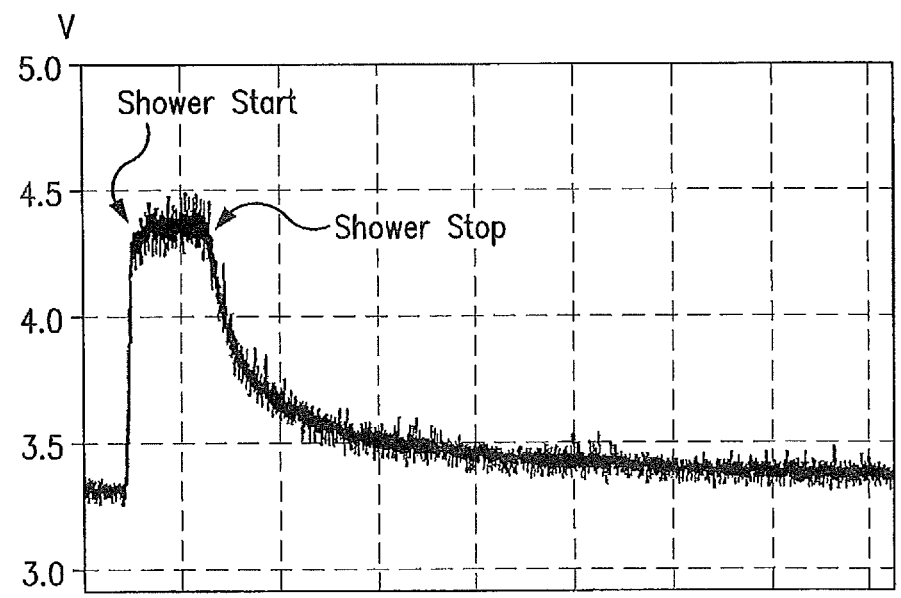
Figure 2A:
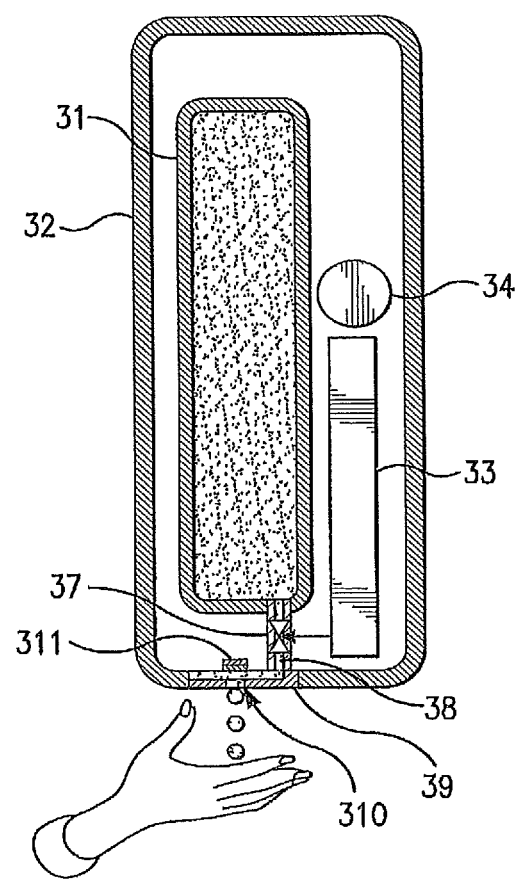
FIG. 2a shows a first example of a self-sensing piezoelectric dispensing device in a second embodiment according to the present invention used in a liquid dispenser with a hand proximity detection.
Figure 2B:
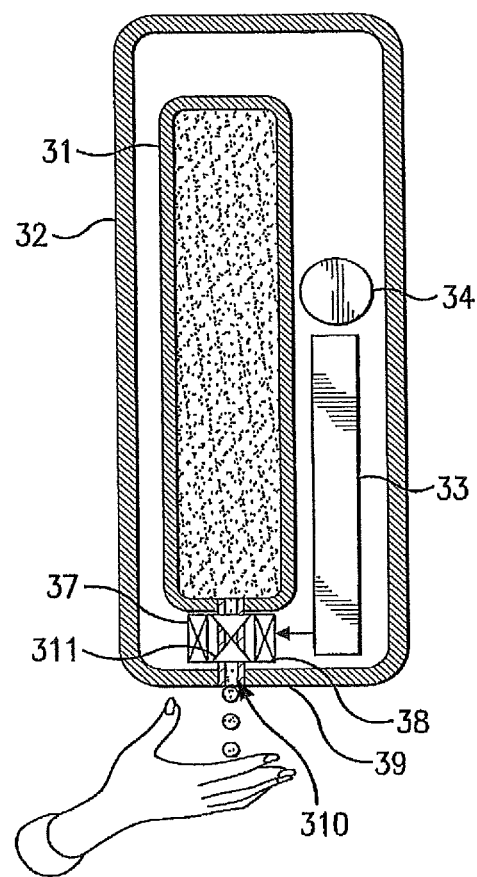
FIG. 2b shows a second example of a self-sensing electromagnetic dispensing device in the second embodiment.
Figure 2C:
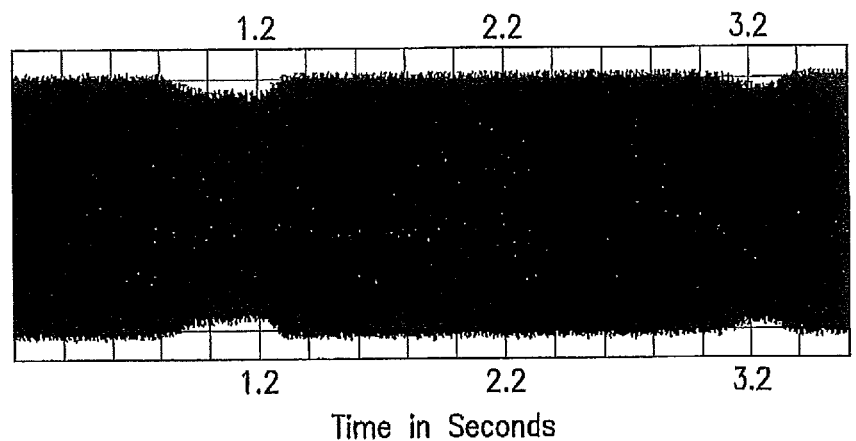
FIGS. 2c and 2d show examples of signals used in the hand proximity detection in the second embodiment.
Figure 2D:
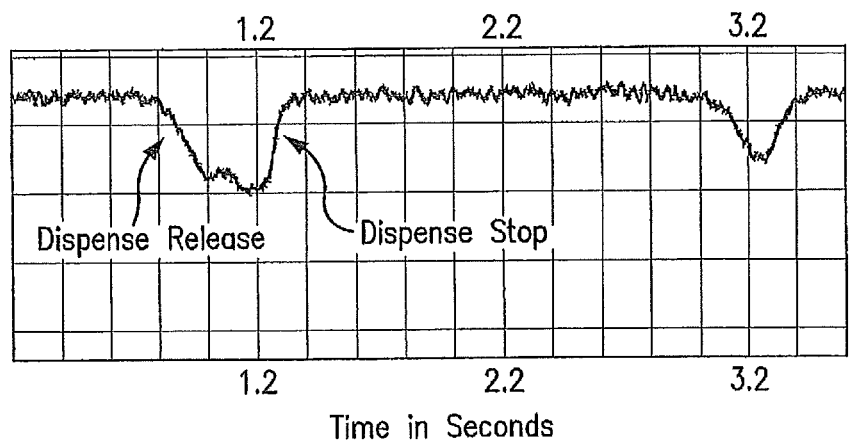

As can be understood from the above, according to the present invention, piezoelectric actuator 11 not only allows liquid to be dispensed, but it also allows to control when, how and which liquid (when using more than one tank) is to be dispensed. In fact, by using the principle of piezoelectricity not only to convert electricity to mechanical movement, but also to convert mechanical perturbations back to electricity, the piezoelectric actuator 11 can be used to detect external characteristics, in this case water flow of the shower, as such water flow creates combined sonic and ultrasonic pressure waves in the proximity of the shower apparatus, which causes perturbation that can be picked up by piezoelectric actuator 11, thus allowing to detect the water flow. By appropriate analysis of the electrical signals resulting from the water flow pressure waves through electronics means 6, it is possible to determine when water flow starts and stops. It is then also possible to control, once the water flow is detected as started, electro-valve 7 so that liquid may be provided from tank 1 to spray head 9 and thus be ejected by self-sensing actuator 11. This control can be carried out by the electronic control means 6, triggered by the self-sensing piezoelectric actuator 11. Thus, a shower apparatus having such a water flow detector can then automatically trigger release of a cleaning, fragrancing or disinfecting substance.

The analysis of the electrical signals resulting from the water flow-generated pressure waves will be explained in more detail with respect to FIGS. 1*c* and 1*d*. As can be seen in FIG. 1*c*, the start and stop of the water flow can be readily detected as the pressure waves detected by piezoelectric actuator 11 increase sharply when water flow starts, and decrease rapidly when the water flow stops. Using this signal, it is possible to apply a threshold detection additional to the above analysis, as shown for example in FIG. 1d, above which a water flow is considered to be in progress. Thus, the start and stop of a water flow can be readily detected by the self-sensing spray head 9.

The piezo-generated electric signal undergoes appropriate filtering in order to reliably isolate the water flow-originated signal from everything else picked-up (i.e. background noise).

Of course, a skilled person can readily conceive other applications, for example in the case of 2 tanks and 2 different liquids, for example a fragrancing and a disinfecting liquid, the self-sensing spray head 9 and the electronic control means 6 may be arranged to allow spraying of the fragrancing liquid during the showering process and the disinfecting liquid some predetermined time after the showering process. It will also be evident to the skilled person that the applications may not be not limited to showers, but that there may be others which use the same self-sensing principle, including applications in household appliances, like laundry dryers, vacuum cleaners, cleaning robots and the like.

A second example of the first embodiment is shown in FIG. 1b where an arrangement is shown that is rather similar to the one in the first example. Same elements are referred to by same reference numerals. In this second example, housing 3 is arranged above tank 1, and thus inlet channel 8 extends into the tank to allow the liquid solution to be drawn out towards spray head 9. As can be understood from this shown configuration, compared to the upside-down configuration of the first example, the configuration of the second example avoids possible leakage of residual liquid after removing tank 1.

A third example of the first embodiment is shown in FIG. 1c where a rather similar arrangement is shown as in the second example. Same elements are referred to by same reference numerals. In this third example, housing 3 is thus also arranged above tank 1. Here, the inlet channel is formed of two parts, a first part 7', which is in this example a wick contained in tank 1, and a second part 8', which may also be a wick, or may be a capillary channel for transporting the liquid provided from tank 1 by way of wick 7' to spray head 9. This example does not use an electro-valve, so that the liquid transfer from tank 1 to spray head 9 is performed by capillarity.

In order to avoid leakage due to the absence of valving means, spray head 9 is positioned such that the hydrostatic pressure at spray head 9 is higher than the hydrostatic pressure in tank 1.

As can be understood from the above, in all examples of this first embodiment, any release of liquid from tank 1, and thus from the dispensing device is controlled by signals provided by the self-sensing piezoelectric actuator.

FIG. 3a shows a first example of a self-sensing piezoelectric dispensing device in a second embodiment according to the present invention used in a liquid dispenser.

In this embodiment, the piezoelectric actuator 311 is also used as a proximity sensor, thus allowing to control release of the substance to be dispensed.

The dispensing device is again rather similar to that of the first embodiment. Thus, a housing 32 is provided comprising a reservoir 31 for containing liquid to be dispensed. Also provided are a battery 34 and electronic control means 33 for controlling the release of liquid, by way of signals sent by the piezoelectric actuator, similar to the functioning in the above-described embodiments.

Thus, here too, any release of liquid from reservoir 31, and thus from the dispensing device is controlled by signals provided by the piezoelectric actuator 311.

Indeed, as can be seen from FIG. 3a, again inlet means are provided for providing a fluidic connection between reservoir 31 and a dispensing element, here dispensing head 39 by way of valving means such as an electro-valve 37. Dispensing head 39 comprises a dispensing aperture 310, for example a spout, having one or more nozzles through which the liquid is to be dispensed. A piezoelectric actuator 311 is also provided in the dispensing head to allow control of electro-valve 37, by detection of the proximity of a hand, and thus of the release of liquid from the reservoir, and ultimately from the dispensing device.

In this embodiment, and indeed in all other embodiments too, the dispenser may be arranged to emit an appropriate electrical signal to detect reflection thereof, by way of analysis of the return signal. As such, any movement, object or presence below the actuator can be detected. Such analysis of a return signal is well known as such to a person skilled in the art.

FIGS. 3c and 3d shows examples of signals used in a hand proximity detection in the second example of the second embodiment.

As can be seen, the proximity and the absence of proximity can be readily detected by appropriate time-frequency analysis of the signals shown in FIG. 3c and FIG. 3d.

As can be understood from the description of the above three embodiments, a smart dispensing device may be obtained by using a self-sensing dispenser.

Actuation can be triggered by an acoustic pressure wave, noise, presence detection or by motion detection.

Additional advantages of the self-sensing dispensing device according to the present invention concern the fact that sensing and dispensing actions are carried out by the same component. In conventional devices, a dispensing device could continue to dispense even when the separate sensor has failed, thus leading to waste of the dispensed liquid.

Clearly, a cheaper device may also be obtained, as no separate sensor needs to be provided, connected and calibrated.

Further, the dispensing device according to the present invention may be provided with self-learning technology. For example, the electronic control means may be provided with a memory for storing detection results and to allow for a self-calibration, by comparing with previously stored detection results. For instance, the electronic control means may analyze the envelope of the command signal generated by the actuator by comparing it with pre-stored signals, the result of this comparison allowing to trigger the actuation means.

Moreover, the present self-sensing piezoelectric dispenser may even detect clogging, as this leads to modification of the electro-mechanical characteristic of the self-sensing piezoelectric dispenser.

Also, an empty detection in the dispenser can be performed in this manner, so the piezoelectric actuator can be stopped.

Having described now the preferred embodiments of this invention, it will be apparent to one of skill in the art that other embodiments incorporating its concept may be used. It is felt, therefore, that this invention should not be limited to the disclosed embodiments, but rather should be limited only by the scope of the appended claims.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. Self-sensing liquid cleaner or fabric softener dispensing device comprising:
   power supply means,
   a liquid dispensing element comprising an actuator and a dispensing aperture through which liquid is to be dispensed by activation of the actuator,
   electronic control means operable to control said actuator,
   liquid supply means for connecting with a liquid reservoir to supply liquid from said reservoir to said liquid dispensing element,
   valving means for allowing or blocking liquid to flow from said reservoir through said liquid supply means to said liquid dispensing element,
   wherein said actuator is operable to execute in itself—at least a dispensing function and a detecting function, the detecting function detecting at least characteristics external to the self-sensing dispensing device and causing said actuator to generate a command signal, and
   wherein said electronic control means is operable to control said valving means and said actuator based on the reception of said command signal.

2. The self-sensing dispensing of claim 1, wherein said electronic control means is operable to open and/or close said valving means based on said command signal.

3. The self-sensing dispensing device of claim 2, wherein said electronic control means is operable to turn on and off said self-sensing dispensing device based on said command signal.

4. The self-sensing dispensing device of claim 1, wherein said electronic control means is operable to analyze a time-frequency response of said command signal, the result of said analysis allowing to trigger said valving means.

5. The self-sensing dispensing device of claim 4, wherein said electronic control means comprises memory means for storing results of said analysis for self-learning purposes.

6. The self-sensing dispensing device of claim 1, wherein said actuator is a piezoelectric actuator.

7. Shower apparatus comprising:
   a showerhead, and
   a water flow detector, wherein said water flow detector consists of the self-sensing dispensing device of claim 6.

8. Liquid cleaner of fabric softener dispenser comprising:
   the self-sensing dispensing device of claim 6,
   said dispensing element having at least one outlet for dispensing said liquid as a flow, and
   said electronic control means and said piezoelectric actuator being arranged to detect presence or movement of an object in the proximity of said piezoelectric actuator.

9. Household appliance comprising the self-sensing dispensing device of claim 6.

10. The self-sensing dispensing device of claim 1, wherein said actuator is an electromagnetic actuator.

11. Liquid cleaner of fabric softener dispenser comprising:
   the self-sensing dispensing device of claim 10,
   said dispensing element having at least one outlet for dispensing said liquid as a flow, and
   said electronic control means and said electromagnetic actuator being arranged to detect presence or movement of an object in the proximity of said electromagnetic actuator.

* * * * *